(12) United States Patent
Overes et al.

(10) Patent No.: US 8,551,121 B2
(45) Date of Patent: Oct. 8, 2013

(54) BI-DIRECTIONAL SUTURE PASSER (75) Inventors: Tom Overes, Langendorf (CH); Robert Frigg, Langendorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 279 days.

(21) Appl. No.: 12/769,234

(22) Filed: Apr. 28, 2010

(65) Prior Publication Data
US 2011/0112555 A1 May 12, 2011

Related U.S. Application Data (60) Provisional application No. 61/173,372, filed on Apr. 28, 2009.

(51) Int. Cl.
*A61B 17/12* (2006.01)

(52) U.S. Cl.
USPC ........................................ 606/145

(58) Field of Classification Search
USPC .................. 606/139, 144, 145, 228, 151, 213
See application file for complete search history.

(56) References Cited

U.S. PATENT DOCUMENTS

| 7,326,221 | B2* | 2/2008 | Sakamoto et al. ............. 606/139 |
| 2006/0253126 | A1* | 11/2006 | Bjerken et al. ................. 606/139 |
| 2011/0112555 | A1 | 5/2011 | Overes et al. |

FOREIGN PATENT DOCUMENTS

| CN | 102365056 | 2/2012 |
| WO | WO 2007/009115 | 1/2007 |
| WO | WO 2010/129312 | 11/2010 |

OTHER PUBLICATIONS

International Patent Application No. PCT/US2010/032672: International Search Report dated Nov. 10, 2010, 9 pages.

* cited by examiner

*Primary Examiner* — Victor Nguyen
(74) *Attorney, Agent, or Firm* — Woodcock Washburn LLP (57) ABSTRACT

A bi-directional suture passing instrument is disclosed. The suture passing instrument may include a housing having a first cannulation and a second cannulation that is spaced from the first cannulation by a tissue receiving gap. The instrument may also include a shuttling element movable across the tissue receiving gap between the first and second cannulations. The shuttling element is configured to carry a strand of suture. A first pusher disposed in the first cannulation is configured to push the shuttling element from the first cannulation toward the second cannulation, and a second pusher disposed in the second cannulation is configured to push the shuttling element from the second cannulation toward the first cannulation.

21 Claims, 12 Drawing Sheets

BI-DIRECTIONAL SUTURE PASSER

CROSS REFERENCE TO RELATED APPLICATIONS

This application claims priority to U.S. Provisional Application No. 61/173,372, filed Apr. 28, 2009, the contents of which are incorporated by reference in their entirety.

BACKGROUND

Lumbar discectomy, a procedure that may treat radiculopathy by surgically removing herniated nucleus pulposus to achieve neural decompression, is a common spinal surgery. Conventional discectomy techniques do not adequately repair an annular defect such as a hole or breach, created in an annulus either pathologically due to a disc herniation, or by the surgeon during the procedure, and presents the surgeon with a dilemma. The surgeon may elect to remove only the herniated portion of the herniated nucleus pulposus impinging on the nerves, which treats the radiculopathy, but increases the risk of post-operative reherniation of the remaining nucleus pulposus within the disc. Alternatively, the surgeon may elect to perform extensive debulking, in which most of the remaining nucleus pulposus material is removed in addition to the herniated portion to minimize the risk of post-operative reherniation; however, the risk of post-operative disc height collapse and resulting lower back pain typically increases.

SUMMARY

In accordance with one aspect of the present disclosure, an annular repair system overcomes technical challenges presented by conventional discectomy procedures and the post-operative potential complications associated therewith. For instance, the annular repair system is able to close or repair a defect in the annulus.

A suture passing instrument configured to approximate and repair soft tissue defects is disclosed. In one embodiment the suture passing instrument may include a housing having a first cannulation and a second cannulation that is spaced from the first cannulation by a tissue receiving gap. The instrument may also include a shuttling element movable across the tissue receiving gap between the first and second cannulations. The shuttling element is configured to carry a strand of suture. A first pusher disposed in the first cannulation is configured to push the shuttling element from the first cannulation toward the second cannulation, and a second pusher disposed in the second cannulation is configured to push the shuttling element from the second cannulation toward the first cannulation.

In another embodiment the suture passing instrument may include a housing having a first cannulation in communication with a second cannulation, and a tissue receiving gap disposed between the first and second cannulations. The instrument may also include a needle that is configured to carry a strand of suture in a first direction from the first cannulation toward the second cannulation, and in a second direction from the second cannulation back toward the first cannulation. The needle defines first and second tissue penetrating ends, such that the first tissue penetrating end penetrates tissue when the needle moves in the first direction, and the second tissue penetrating end penetrates tissue when the needle moves in the second direction.

In another embodiment the suture passing instrument may include a housing having a first cannulation in communication with a second cannulation having a curved portion, and a tissue receiving gap disposed between the first and second cannulations. The instrument also includes a flexible shuttling element configured to carry a strand of suture between the first cannulation and the second cannulation. The shuttling element is also configured to bend and conform to the curved portion of the second cannulation.

Methods of operating the different embodiments of the suture passing instrument are also disclosed. For example, in one embodiment, the needle may be pushed in a first direction from the first cannulation towards the second cannulation. As the needle is being pushed in the first direction, a first end of the needle penetrates a piece of tissue. The needle may then be pushed in a second direction from the second cannulation toward the first cannulation. As the needle is being pushed in the second direction, a second end of the needle penetrates the piece of tissue.

BRIEF DESCRIPTION OF THE DRAWINGS

The foregoing summary, as well as the following detailed description of a preferred embodiment of the application, will be better understood when read in conjunction with the appended drawings. For the purposes of illustrating the bidirectional suture passer instrument of the present application, there is shown in the drawings referred embodiments. It should be understood, however, that the application is not limited to the precise arrangements and instrumentalities shown. In the drawings.

DETAILED DESCRIPTION OF ILLUSTRATIVE EMBODIMENTS

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the bidirectional suture passer instrument and related parts thereof. The words, "anterior", "posterior", "superior," "inferior", "lateral", "medial" and related words and/or phrases designate preferred positions and orientations in the human body to which reference is made and are not meant to be limiting. The terminology includes the above-listed words, derivatives thereof and words of similar import.

Figure 1:
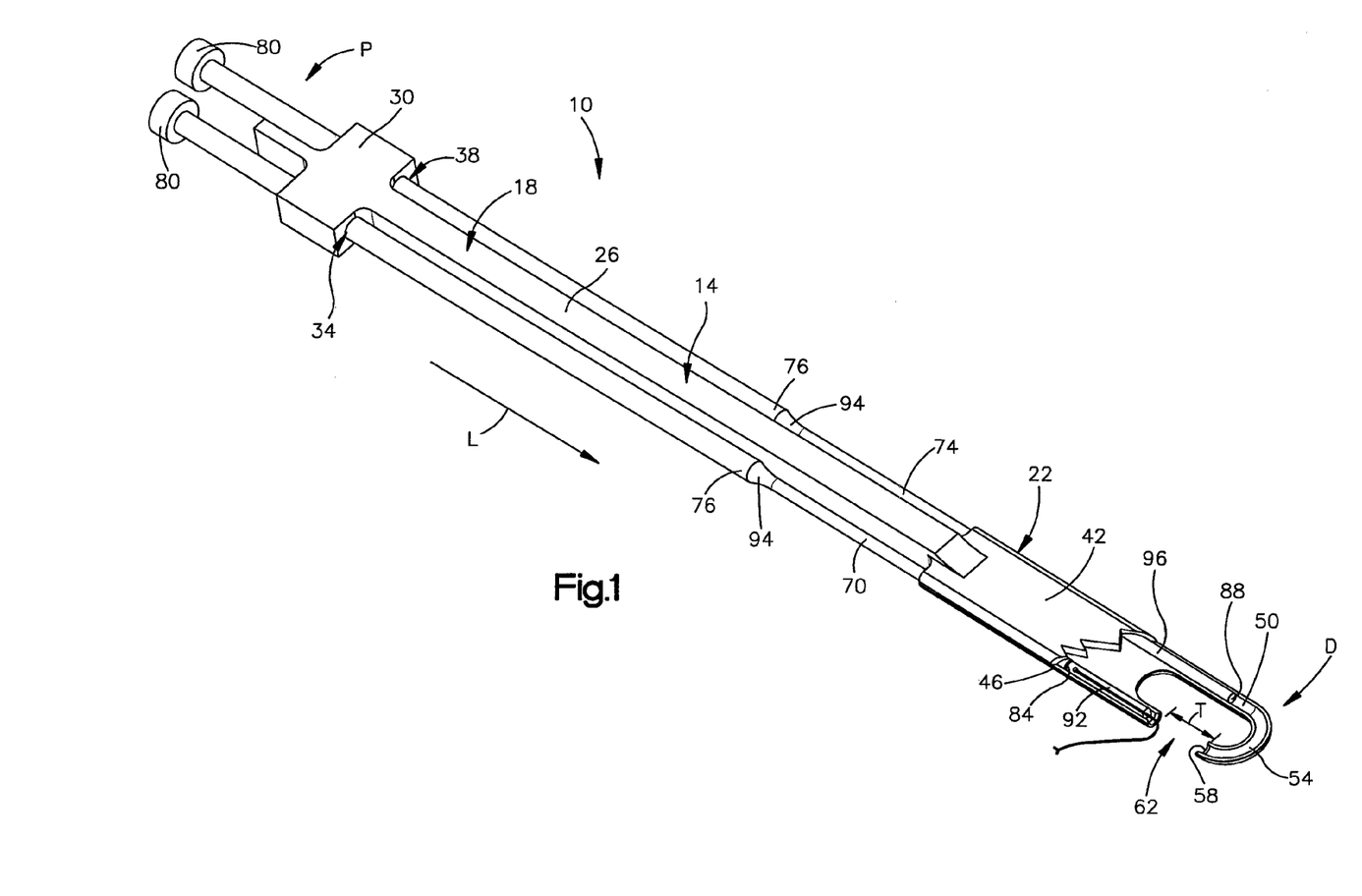
FIG. 1 is a top perspective view of a suture passer instrument constructed in accordance with one embodiment, having a portion cut away.

Referring to FIG. 1, a bidirectional suture passer instrument 10 is elongate along a longitudinal direction L that separates a proximal end P of the suture passer 10 from an opposed distal end D of the suture passer 10. As shown, the instrument 10 includes a longitudinally elongate housing 14 having a proximal portion 18, and an opposed distal portion 22. The proximal portion 18 of the elongated housing 14 includes a body member 26 that is elongate in the longitudinal direction L, and a transverse body member 30 extending transversely across a proximal end of the body member 26. The transverse body member 30 defines a first longitudinal bore 34 that extends longitudinally through a lower portion of the transverse body member 30, and a second longitudinal bore 38 that extends longitudinally through an upper portion of the transverse body member 30.

The distal portion 22 of the housing 14 includes a body 42 that extends distally from a distal end of the body member 26. As shown, the body 42 includes a first cannulation 46 that extends longitudinally through a lower portion of the body 42, and a second cannulation 50 that extends longitudinally through an upper portion of the body 42. A proximal end of the first cannulation 46 is in operative alignment with (and, in the illustrated embodiment, is aligned with) the first bore 34 that extends through the transverse body member 30, and a proximal end of the second cannulation 50 is in operative alignment with (and, in the illustrated embodiment, is aligned with) the second bore 38 that extends through the transverse body member 30. As shown in FIG. 1, the second cannulation 50 curves as it extends distally to define a curved portion 54. The curved portion 54 defines a U-shaped track that extends around the body 42 such that an open end 58 of the curved portion 54 extends toward and is in communication with the first cannulation 46. That is the open end 58 is in operative alignment with the first cannulation 46. A tissue receiving gap 62 is disposed between the first cannulation 46 and the open end 58 of the curved portion 54. The tissue receiving gap 62 has a longitudinal length T, and is configured to be applied over soft tissue that is in need of repair and adjacent a tissue defect, such as a fissure of the annulus fibrosus of an intervertebral disc (not shown).

As shown in FIG. 1, the suture passer 10 also includes a first pusher 70 and a second pusher 74 translatably coupled to the housing 14. In particular, the first pusher 70 is coupled to and translatable within the first bore 34 of the transverse body member 30 and the first cannulation 46, and the second pusher 74 is coupled to and translatable within the second bore 38 of the transverse body member 30 and the second cannulation 50. Because the first pusher is configured to translate within the first bore 34 and the first cannulation 46, the bore 34 and the cannulation 46 can be said to be in operative alignment. Likewise, because the second pusher 74 is configured to translate within the second bore 38 and the second cannulation 50, the bore 38 and the cannulation 50 can be said to be in operative alignment. Preferably the second pusher 74 is disposed parallel to the first pusher 70. While the first and second pushers 70, 74 are shown as separate structures, it should be understood that the first and second pushers 70 and 74 may be connected at their proximal ends thereby creating a single unitary pusher. An example of such an embodiment is described with respect to FIGS. 14-22.

The first and second pushers 70 and 74 each include an elongated body 76 having a proximal end and a distal end. The proximal ends of the first and second pushers 70, 74 preferably include handle portions or engagement features 80 that can receive a pushing force that biases the pushers 70 and 74 proximally and/or distally. The distal ends of the first and second pushers 70 and 74 include a first pusher end 84 and a second pusher end 88 respectively. Preferably, the first and second pushers 70 and 74 define respective recesses, or hollow portions at their respective ends 84 and 88. The recess is illustrated as a conical recess, though the recess can be alternatively shaped. The recesses 84 and 88 are configured to receive the opposed ends of a shuttling element 92. The body 76 of each pusher 70 and 74 also includes a shoulder portion 94 disposed proximal to the distal portion 22 of the housing 14. The shoulder portions 94 are configured to limit the travel of the first and second pushers 70 and 74.

Figure 9:
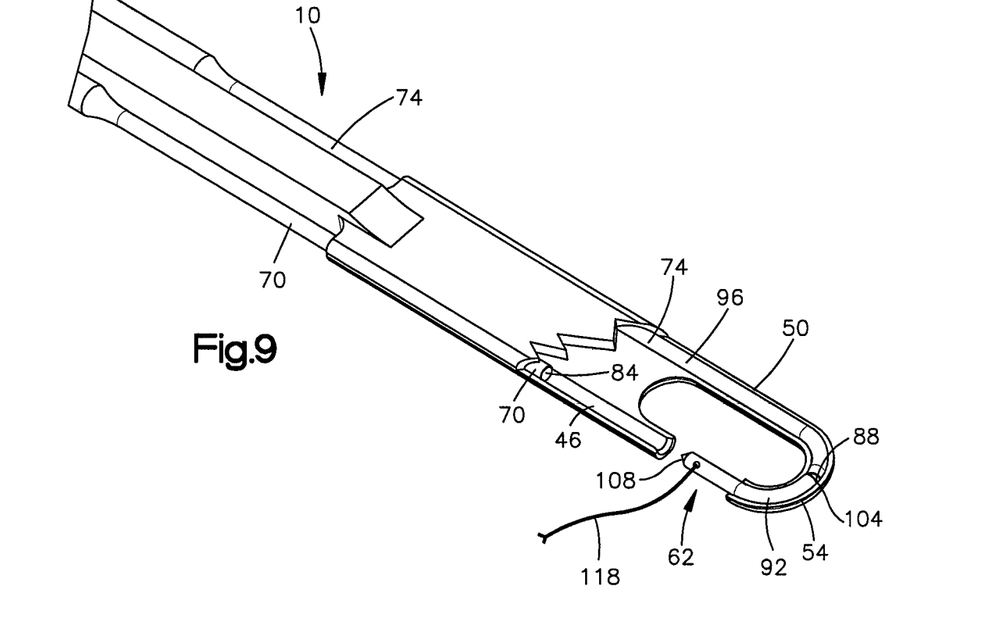
FIG. 9 is an enlarged perspective view similar to FIG. 7, but showing the distal end in a configuration where the first pusher is fully retracted within the first cannulation, the shuttling element is being passed back across a gap and the second pusher is partially advanced still further distally within the second cannulation and into the curved portion of the second cannulation.
Figure 10:
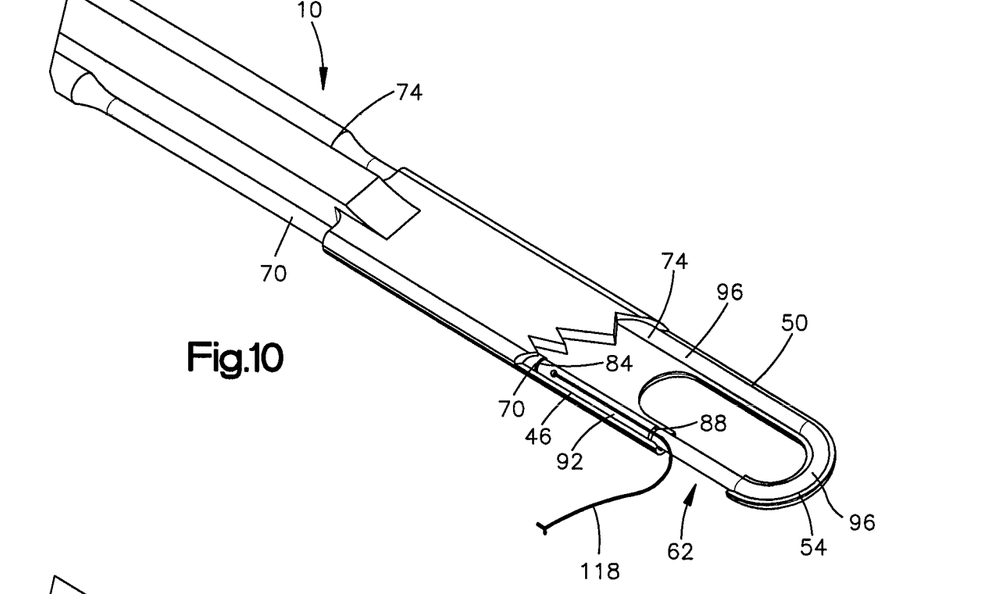
FIG. 10 is an enlarged perspective view similar to FIG. 9, but showing the distal end in a configuration where the first pusher is fully retracted within the first cannulation, the shuttling element is fully retracted within the first cannulation, and the second pusher is fully advanced within the second cannulation.
Figure 11:
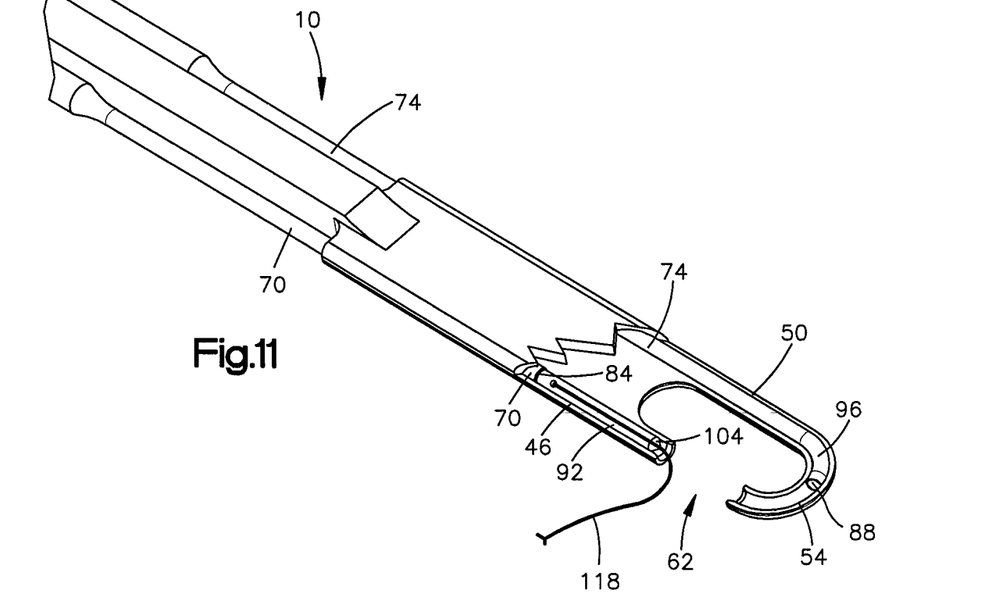
FIG. 11 is an enlarged perspective view similar to FIG. 10, but showing the distal end in a configuration where the first pusher is fully retracted within the first cannulation, the shuttling element is fully retracted within the first cannulation, and the second pusher is retracted proximally within the second cannulation.

At least a portion of the body 76 of the second pusher 74 is flexible. In accordance with the illustrated embodiment, the body 76 includes a rigid portion and a flexible portion. The rigid portion and the flexible portion may be separate pieces coupled together or one unitary piece. As shown in FIGS. 9-11, a distal portion 96 of the second pusher 74 is flexible and is formed of an elastic or super elastic material having shape memory characteristics, such as Nitinol, that allows the distal portion 96 of the second pusher 74 to bend as it advances along the curved portion 54 of the second cannulation 50 as a result of a distal translation of the second pusher 74 with respect to the housing 14. The flexible distal portion 96 of the second pusher 74 is not limited to being made of Nitinol and may be formed of any other material having sufficient elastic properties, for example, a generally flexible polymeric material. The flexible portion of the second pusher 74 may be constructed of a rigid material such as titanium, stainless steel, a variety of suitable plastics, etc. While the second pusher end 88 is part of the flexible distal portion 96, it should be understood that the second pusher end 88 may also be constructed of a rigid material, so long as it is capable of advancing through the curved portion 54 of the second cannulation 50.

The body 76 of the first pusher 70, on the other hand, is intended to remain straight at all times and, thus, may be constructed of a rigid material such as titanium, stainless steel, a variety of suitable plastics, etc. Though it should be understood that the first pusher may be made of any suitable material configured to push the shuttling element 92.

Figure 6:
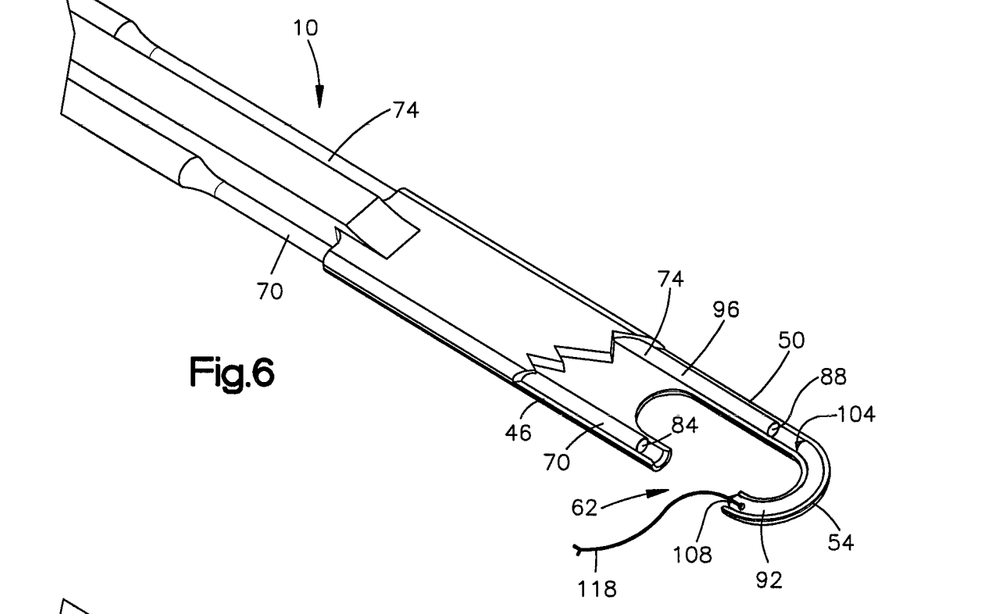
FIG. 6 is an enlarged perspective view similar to FIG. 5, but showing the distal end in a configuration where the first pusher is partially retracted within the first cannulation, and the shuttling element is retained within the curved portion of the second cannulation.

The suture pusher 10 further includes a shuttling element 92 that is configured to move from the first cannulation 46 across the tissue receiving gap 62, and into the curved portion 54 of the second cannulation 50. As best shown in FIG. 6, the shuttling element 92 includes an elongated body 100 that defines a double-tipped flexible needle. In that regard, the body 100 includes a first tissue penetrating end 104 and an opposing second tissue penetrating end 108. Each end 104 and 108 defines a pointed tip that is configured to penetrate and pass through a piece of tissue. The pointed first and second ends 104 and 108 are also configured to be engagable with the conical recesses of the first and second pusher ends 84, 88 of the first and second pushers 70, 74. Thus, as the first pusher 70 is translated distally, the first pusher end 84 engages (or otherwise applies a force to, either directly or indirectly) the first end 104 of the shuttling element 92 to thereby push the shuttling element 92 distally such that the second end 108 of the shuttling element 92 penetrates a piece of tissue disposed within the tissue receiving gap 62. Similarly, as the second pusher 74 is translated distally, the second pusher end 88 engages the second end 108 of the shuttling element 92 to thereby push the shuttling element 92 proximally such that the first end 104 of the shuttling element 92 penetrates the piece of tissue disposed within the tissue receiving gap 62. To ensure that the shuttling element does not fall through the tissue receiving gap 62 as it is being moved across the gap 62, the shuttling element 92 in accordance with the illustrated embodiment has a length S that is greater than the length T of the gap 62.

The shuttling element 92 can be constructed of a flexible material that allows the shuttling element 92 to follow the curved portion 54 of the second cannulation 50. In particular, the shuttling element 92 can be formed of an elastic or super elastic material having shape memory characteristics, such as Nitinol, that allows the shuttling element 92 to bend as it advances along the curved portion 54 of the second cannulation 50 as a result of the first pusher 70 moving the shuttling element 92 distally with respect to the housing 14. It should be understood that the shuttling element 92 is not limited to being made of Nitinol and may be formed of any other material having sufficient elastic properties, for example, a generally flexible polymeric material.

The shuttling element 92 also includes a suture holder such as an eyelet 114 configured to be threaded with a strand of suture 118 that is configured to repair the defect, as will be described in greater detail below. As shown, the eyelet 114 is disposed adjacent to the first end 104 of the shuttling element 92, though it should be understood that the eyelet 114 can alternatively be disposed anywhere along the shuttling element 92.

In operation, and in reference to FIGS. 2-12, the strand of suture 118 is threaded through the eyelet 114 and the shuttling element 92 is loaded into the bidirectional suture passer 10. That is, the shuttling element 92 is inserted into the suture passer instrument 10 so that it is disposed in either the first cannulation 46 or the second cannulation 50. The bidirectional suture passer 10 may be preassembled with the suture strand 118 threaded through the eyelet 114 and the shuttling element 92 loaded into the bidirectional suture passer 10 such that the surgeon or an assistant does not assemble the suture strand 118 onto the bidirectional suture passer 10.

Figure 2:
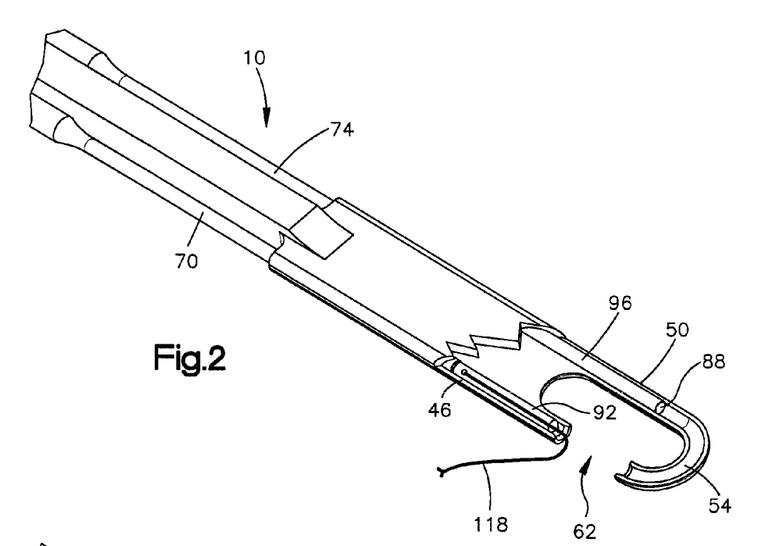
FIG. 2 is an enlarged perspective view of the suture passer instrument of FIG. 1 showing a distal end of the suture passer in a configuration where first and second pushers fully retracted within respective first and second cannulations of a suture passer housing.
Figure 3:
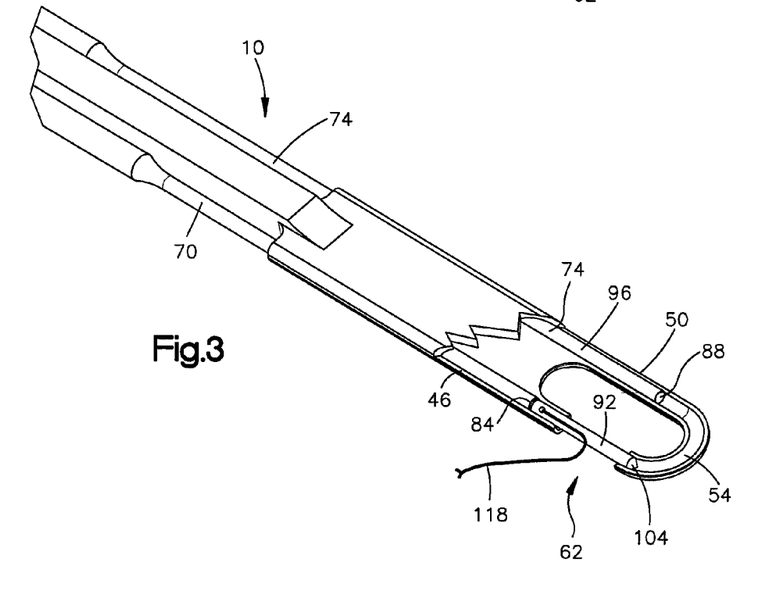
FIG. 3 is an enlarged perspective view similar to FIG. 2, but showing the distal end in a configuration where the first pusher is partially advanced distally within the first cannulation of the housing.
Figure 4:
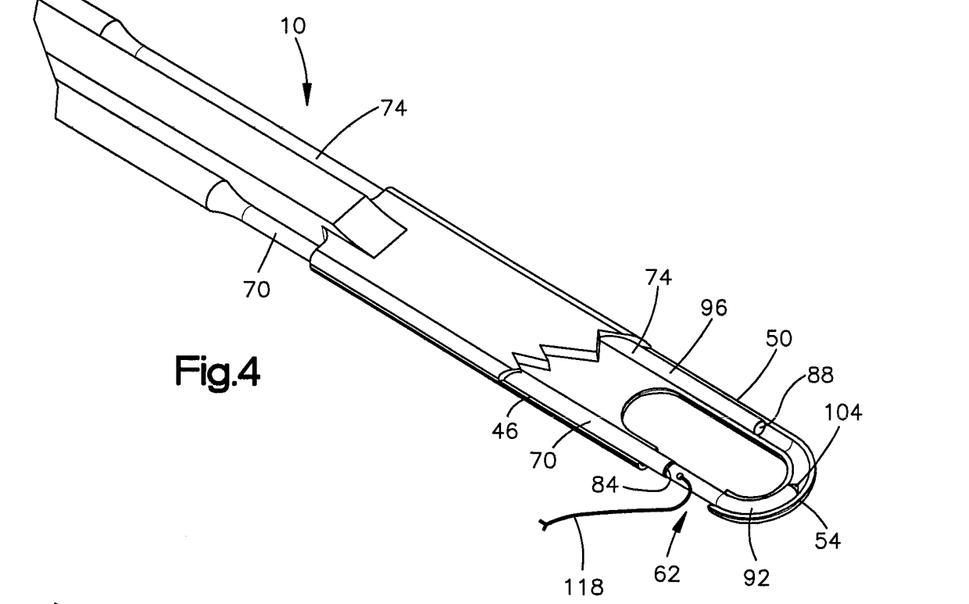
FIG. 4 is an enlarged perspective view similar to FIG. 3, but showing the distal end in a configuration where the first pusher is advanced further distally within the first cannulation of the housing.
Figure 5:
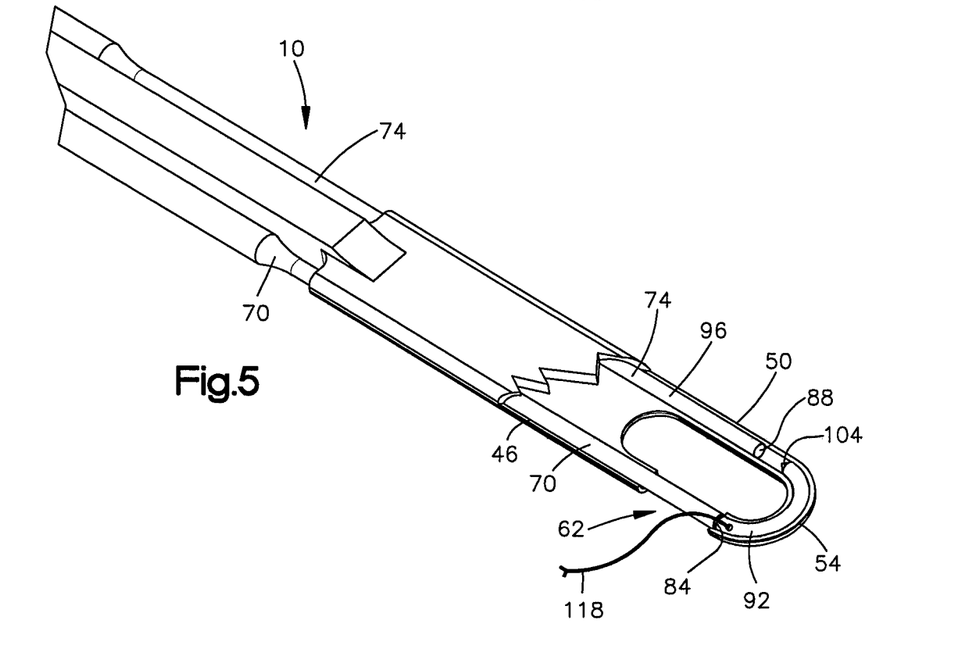
FIG. 5 is an enlarged perspective similar to FIG. 4, but showing the distal end in a configuration where the first pusher is advanced fully distally within the first cannulation, and a shuttling element is retained within a curved portion of the second cannulation of the housing.

As shown in FIG. 2, the first and second pushers 70, 74 are fully retracted with respect to the housing 14 and the first and second cannulations 46 and 50, such that the gap 62 is at least partially open. The tissue in need of repair is then loaded into the gap 62. For example, for an annulus fibrosus having a fissure, the annulus fibrosus tissue adjacent the defect is inserted into the tissue receiving gap 62 of the suture passer 10. The first pusher 70 is then advanced distally by a biasing force, with respect to the housing 14 causing the recessed first pusher end 84 of the first pusher 70 to engage the pointed first end 104 of the shuttling element 92. As shown in FIGS. 3 and 4, as the first pusher 70 is advanced distally, the shuttling element 92, including the suture strand 118, are forced to fully traverse the gap 62 and the soft tissue disposed therein, and into the curved portion 54 of the second cannulation 50. As shown in FIG. 4, the shuttling element 92 bends and conforms to the curved portion 54 as it is advanced into the curved portion 54. When the first pusher 70 is fully advanced, the shuttling element is fully disposed in the curved portion 54 of the second cannulation 50, as shown in FIG. 5.

Figure 7:
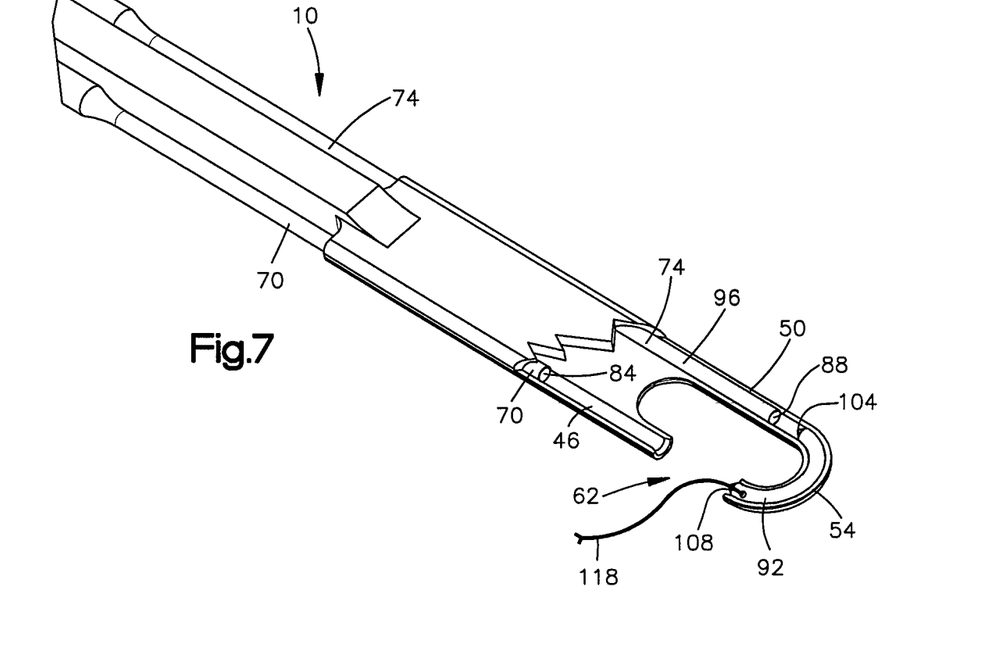
FIG. 7 is an enlarged perspective view similar to FIG. 6, but showing the distal end in a configuration where the first pusher is fully retracted within the first cannulation, the shuttling element is retained within the curved portion of the second cannulation, and the second pusher is partially advanced distally within the second cannulation.
Figure 8:
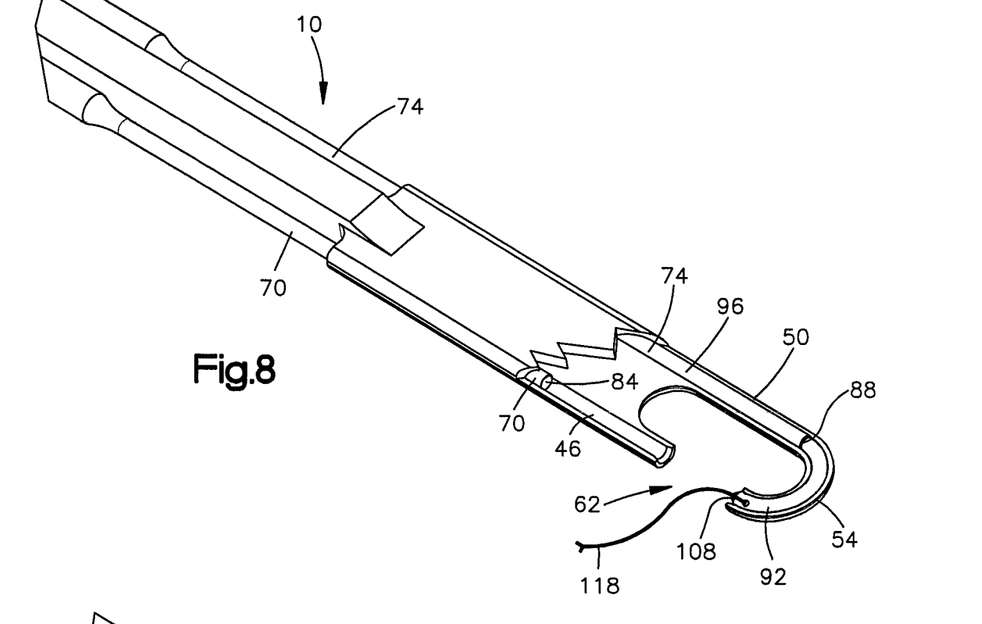
FIG. 8 is an enlarged perspective view similar to FIG. 7, but showing the distal end in a configuration where the first pusher is fully retracted within the first cannulation, the shuttling element is retained within the curved portion of the second cannulation, and the second pusher is partially advanced further distally within the second cannulation.

As shown in FIGS. 6-7, the first pusher 70 is then retracted proximally, by a biasing force, with respect to the housing 14 to a point at which the gap 62 is fully open while the shuttling element 92, and the suture strand 118 remain in the curved portion 54 of the second cannulation 50. The bidirectional suture passer 10 is then rotated or moved a small amount with respect to the defect to accommodate a reverse pass of the shuttling element 92 and suture 118 through the gap 62. As shown in FIGS. 8-10, the second pusher 74 is then fully advanced, by a biasing force, with respect to the housing 14, such that the recessed second pusher end 88 of the second pusher 70 engages the pointed second end 108 of the shuttling element 92 and forces the shuttling element 92 to advance back proximally across the gap 62 and into the first cannulation 46. In particular, the second pusher end 88 and the flexible distal portion 96 are advanced into the curved portion 54 of the second cannulation 50 to thereby force the shuttling element 92 to traverse the gap 62 or at least the soft tissue disposed therein and move back into the first cannulation 46 proximate to the first pusher end 84 of the first pusher 70. It should be understood that the shuttling element 92 does not have to fully traverse the gap so long as it traverses the tissue received within the gap 62.

Figure 12:
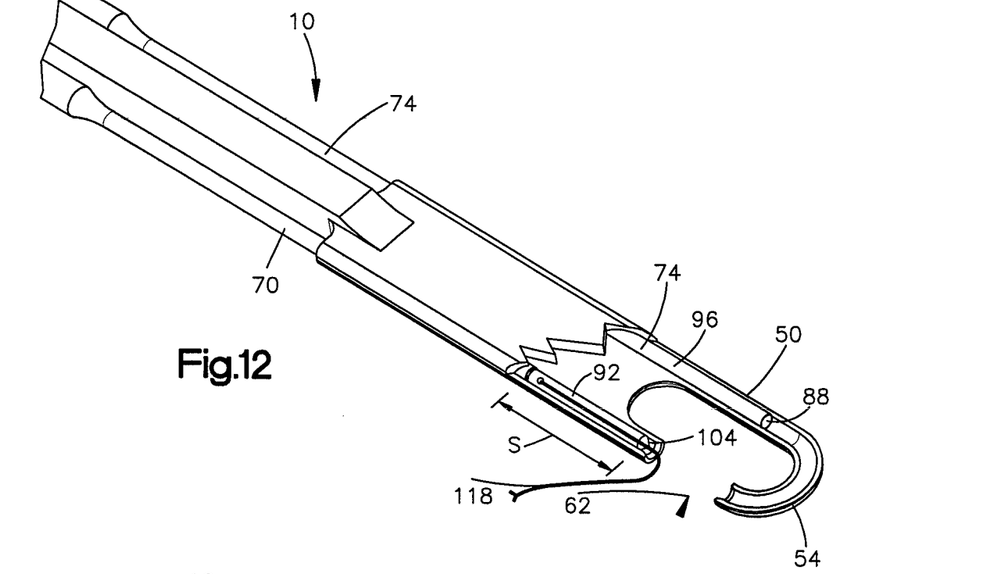
FIG. 12 is an enlarged perspective view similar to FIG. 11, but showing the distal end in a configuration where both pushers are fully retracted within the first and second cannulations.

As shown in FIGS. 11-12, the second pusher 74 may then be retracted proximally, by a biasing force, with respect to the housing 14 such that the gap 62 is fully open (save for the soft tissue retained therein) and such that the bidirectional suture passer 10 is in its initial configuration (step 1, FIG. 2). The bidirectional suture passer 10 is then oriented in a new location with respect to the soft tissue defect, such as by translating or rotating the bidirectional suture passer 10 with respect to the defect, to position a different portion of the soft tissue proximate the defect in the gap 62. The process is repeated one or more times until the tissue is adequately approximated at the defect.

While it is shown in the drawings that the first and second pushers 70, 74 are configured to be biased manually with respect to the housing 14, it is envisioned that a variety of actuation mechanisms can easily be utilized, including automatic, hydraulic, pneumatic, electrical, magnetic, etc to bias the pushers. Further, the bidirectional suture passer 10 may be arranged to have a trigger mechanism to actuate the first and second pushers 70, 74.

Figure 13:
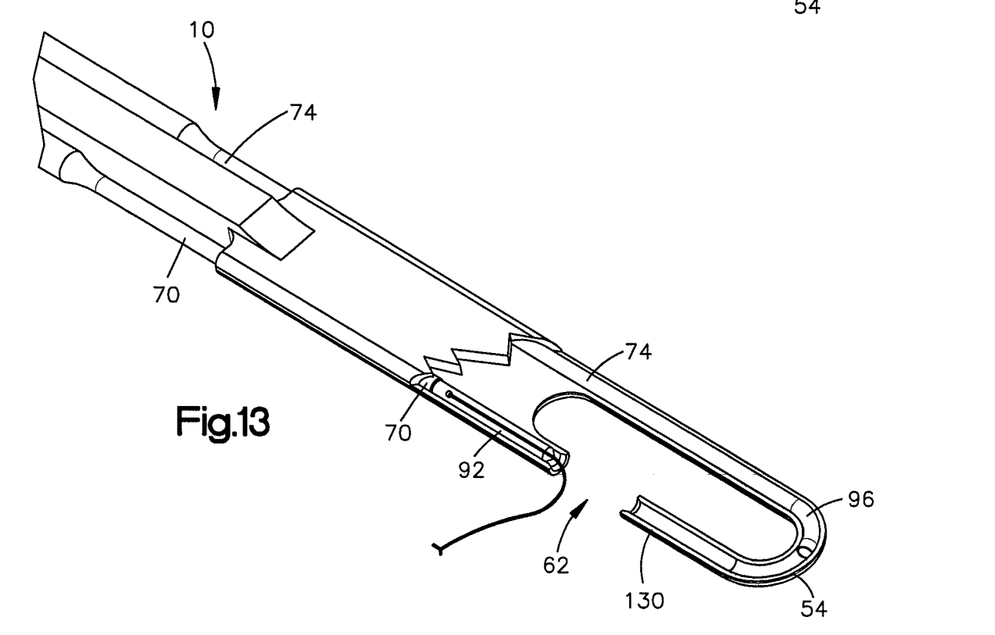
FIG. 13 is an enlarged perspective view similar to FIG. 12, but showing the suture passer instrument having an extended portion that extends from the curved portion of the second cannulation.

As shown in FIG. 13, the second cannulation may include an extended portion 130 that extends proximally from the curved portion 54. As shown, the extended portion 130 is in-line with the first cannulation 46 and is substantially straight. In embodiments having the extended portion 130, the shuttling element 92 may be disposed in the extended portion 130, when the shuttling element 92 is moved from the first cannulation 46 to the second cannulation 50. Because the shuttling element 92 will not have to conform to the curved portion 54, the shuttling element may be made from a rigid material.

FIGS. 14-22 show another embodiment of a suture passer 10 in which a single pusher translates the suture strand from the first cannulation 46, across the tissue receiving gap 62 and into the second cannulation 50 of the housing 14. As shown, the suture passer 10 may include a single pusher 150 configured to push a shuttling element 155 across the tissue receiving gap 62. However, it should be understood that because there is only a single pusher 150, eventually the user begins to pull the pusher 150 rather than push, and thus, it may also be said that the shuttling element 155 is pulled across the tissue receiving gap 62.

The pusher 150 includes a body 158, a first tissue penetrating end 162 extending from a distal end of the pusher body 158, and an opposed second tissue penetrating end 166 extending from a proximal end of the pusher body 158. The body 158 is generally cylindrical and elongate in the longitudinal direction L. Each tissue penetrating end 162, 166 includes a needle point 170 and an inner shoulder 174. Each shoulder 174 is cylindrical and has a diameter that is larger than the diameter of the pusher body 158. The shoulders 174 of the tissue penetrating ends 162, 166 define opposing contact surfaces 178, which can best be seen in FIGS. 14 and 15.

The pusher 150 is configured to translate within both the first cannulation 46 and the second cannulation 50, including the curved portion 54 of the second cannulation 50. Therefore, the body 158 of the pusher 150 is flexible and is formed of an elastic or super elastic material having shape memory characteristics, such as Nitinol, that allows the body 158 of the pusher 150 to bend as it advances along the curved portion 54 of the second cannulation 50 as a result of a distal translation of the pusher 150 with respect to the housing 14. The flexible pusher body 158 is not limited to being made of Nitinol and may be formed of any other material having sufficient elastic properties, for example, a generally flexible polymeric material. The tissue penetrating ends 162, 166 of the pusher 150 may be constructed of a rigid material such as titanium, stainless steel, a variety of suitable plastics, etc.

As shown in FIGS. 14-22, the suture pusher 10 further includes a shuttling element 155 that is slidably coupled to the pusher body 150 between the tissue penetrating ends 162, 166. The shuttling element 155 is configured to move from the first cannulation 46 across the tissue receiving gap 62, and into the second cannulation 50 as the pusher 150 is translated.

Figures 15, 16:
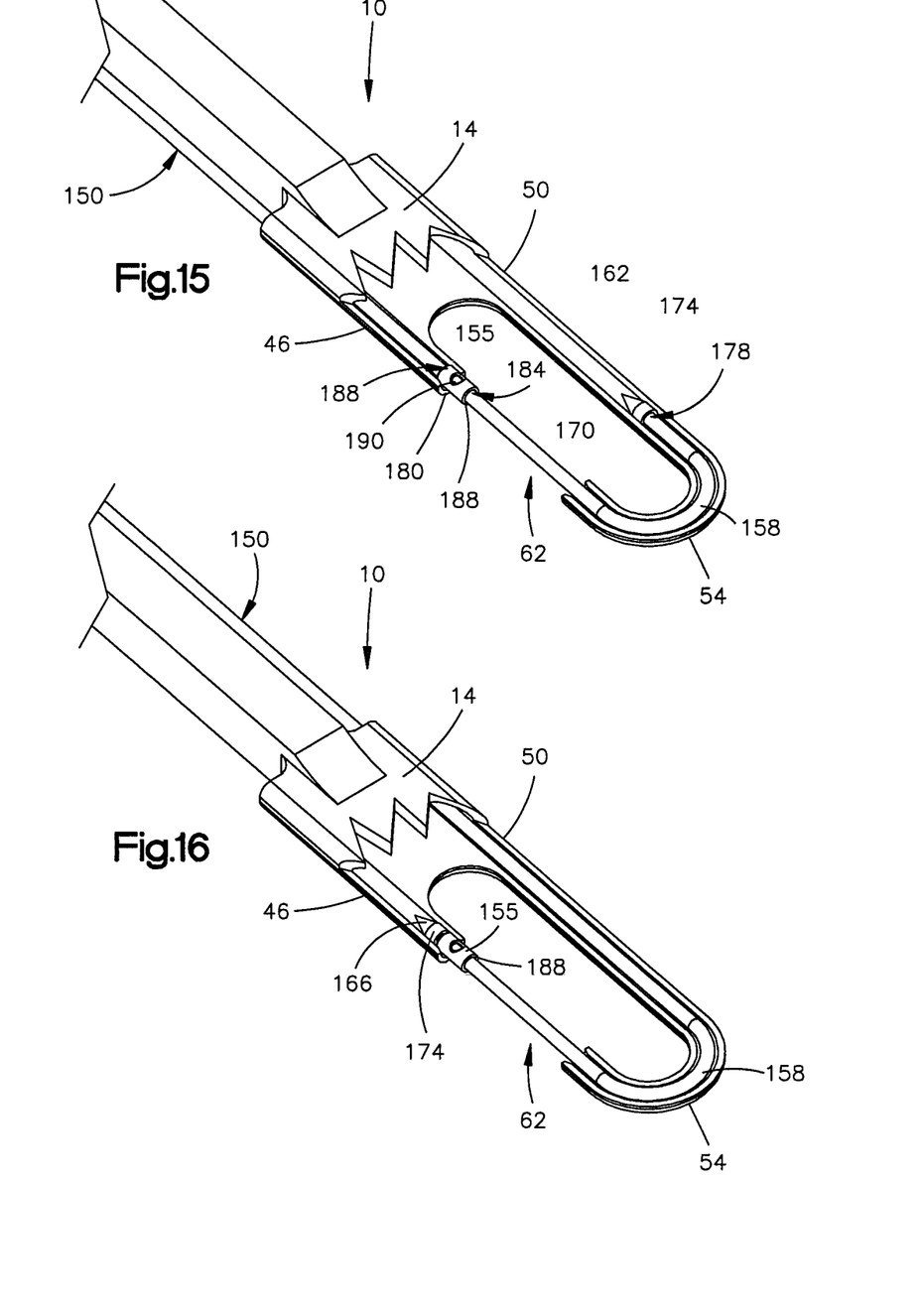
FIG. 15 is an enlarged perspective view of the suture passer instrument of FIG. 14 showing the distal end of the suture passer instrument in an original configuration where the pusher is partially advanced distally within suture passer housing.
FIG. 16 is an enlarged perspective view similar to FIG. 15, but showing the distal end in a configuration where the pusher is advanced distally within the housing such that a second end of the pusher abuts the shuttling element.

As shown, the shuttling element 155 includes a body 180 that is elongate in the longitudinal direction L. As best shown in FIG. 15, the body 180 defines an elongate bore 184 that extends entirely through the body 180. The bore 184 has a diameter that is larger than the diameter of the pusher body 158. Therefore, the shuttling element 155 is capable of sliding along the pusher body 158 as the pusher 150 is translated. The shuttling element body 180 further defines contact surfaces 188 at its distal and proximal ends. Each contact surface 188 of the shuttling element 155 corresponds to a respective contact surface 178 of the pusher's tissue penetrating ends 162, 166. Thus, as the pusher 150 is translated distally in a first direction through the first cannulation 46, and into the second cannulation 50, the shuttling element 155 will remain stationary until the contact surface 188 of the shuttling element's proximal end contacts the contact surface 178 of the second tissue penetrating end 166 of the pusher 150. As the pusher 150 is further translated, the shuttling element 155 is pushed/pulled across the tissue receiving gap 62 by the second tissue penetrating end 166 of the pusher 150. Similarly, as the pusher 150 is translated distally in a second direction that is opposite to the first direction, the shuttling element 155 again remains stationary until the contact surface 188 of the shuttling element's distal end contacts the contact surface 178 of the first tissue penetrating end 162 of the pusher 150. As the pusher 150 is further translated, the shuttling element 155 will be pushed/pulled across the tissue receiving gap 62 by the first tissue penetrating end 162 of the pusher 150.

The shuttling element 155 also includes a suture holder such as an eyelet 190 configured to be threaded with a strand of suture for repairing the defect, as will be described in greater detail below. It should be understood, however, that the suture holder may be an external surface defined by the body 180 of the shuttling element 155 about which the strand of suture is tied.

In operation, and in continuing reference to FIGS. 14-22, the strand of suture is threaded through the eyelet 190 and the shuttling element 155 is loaded onto the body 158 of the suture passer 10. The bidirectional suture passer 10 may be preassembled with the suture strand threaded through the eyelet 190 and the shuttling element 155 loaded onto the pusher 150 such that the surgeon or an assistant is not required to assemble the suture strand onto the bidirectional suture passer 10.

Figure 14:
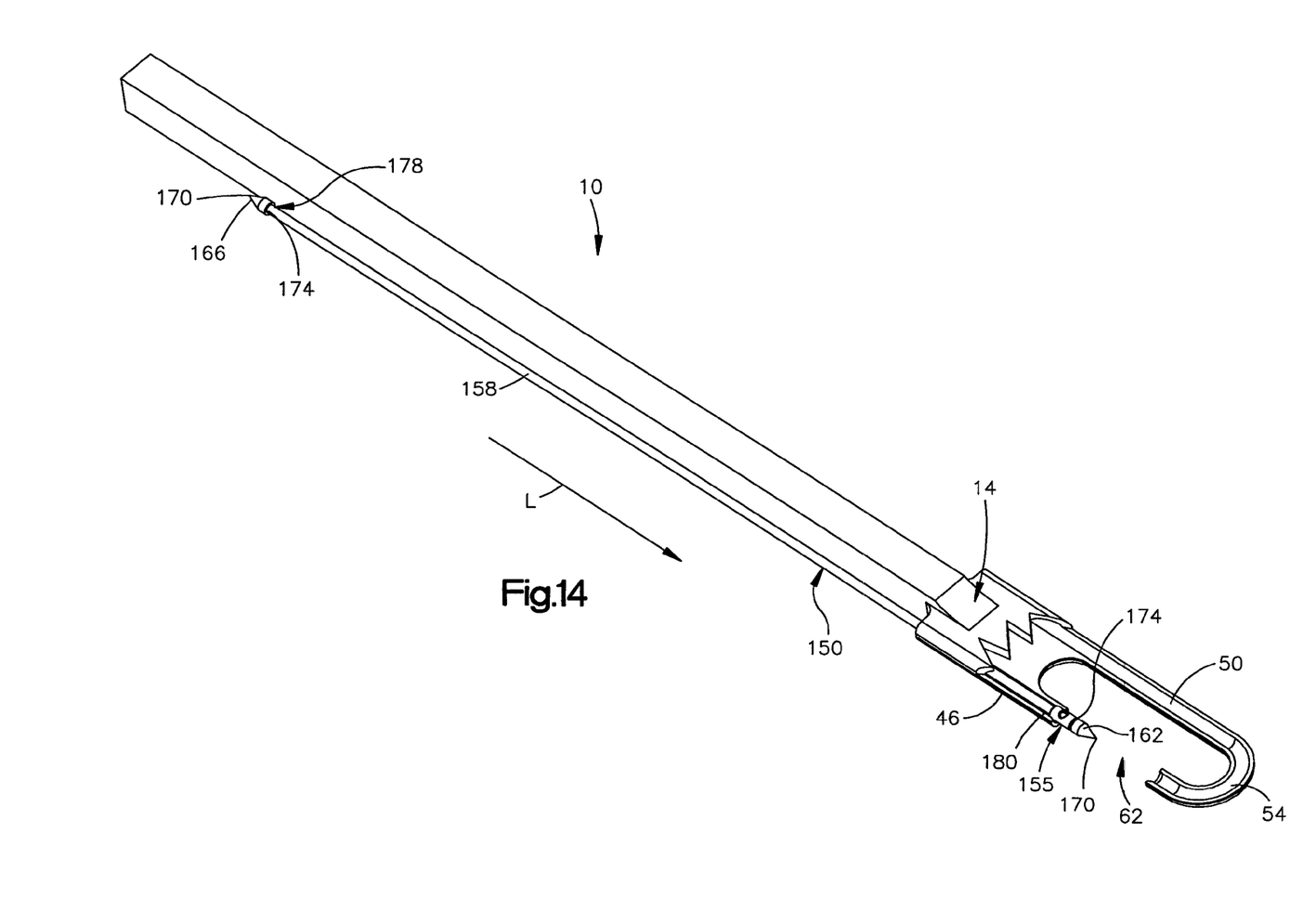
FIG. 14 is a top perspective view of a suture passer instrument constructed in accordance with another embodiment, having a portion cut away the suture passer instrument having a housing that defines opposing proximal and distal portions, and a pusher that is configured to move a shuttling element within the housing.
Figure 17:
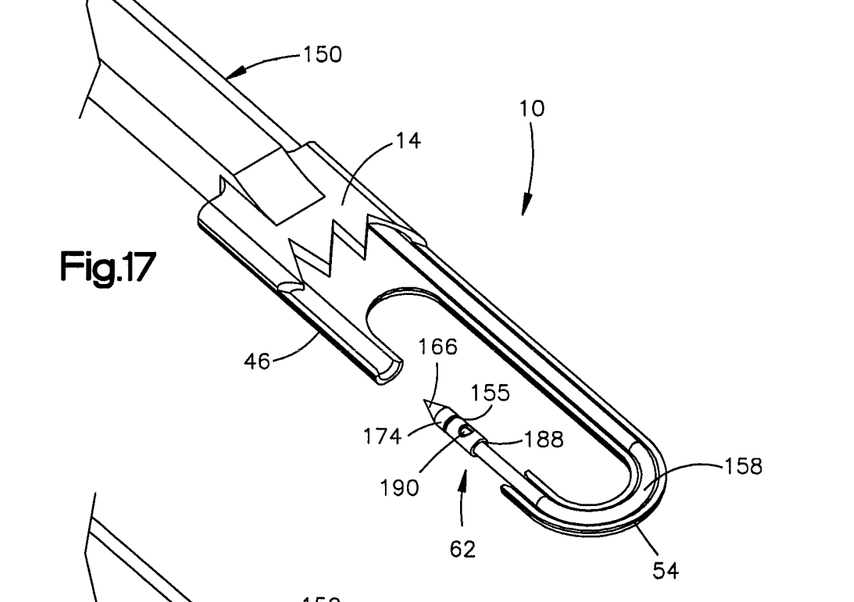
FIG. 17 is an enlarged perspective view similar to FIG. 16, but showing the distal end in a configuration where the pusher pushes the shuttling element across the tissue receiving gap.
Figure 18:
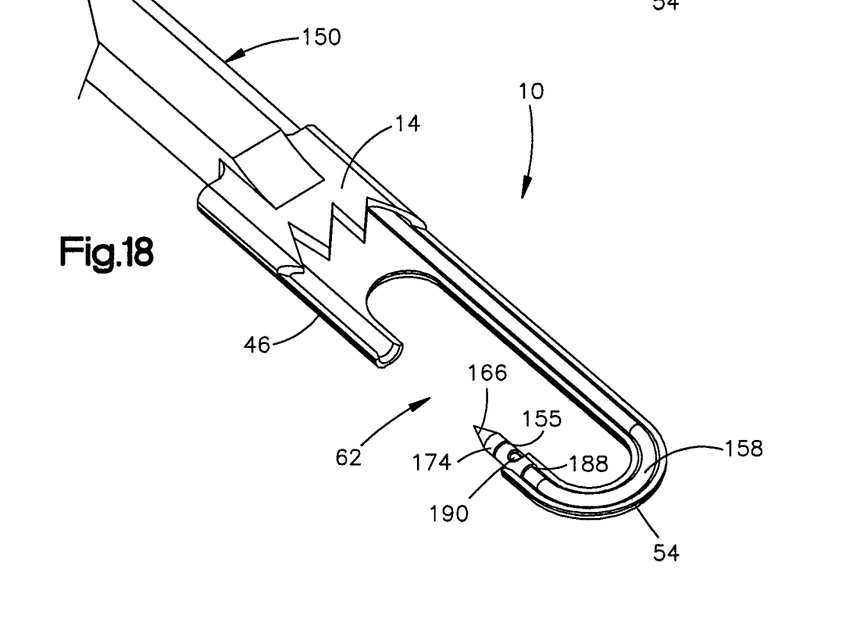
FIG. 18 is an enlarged perspective view similar to FIG. 17, but showing the distal end in a configuration where the pusher is fully advanced such that the shuttling element is on a distal end of a tissue receiving gap defined by the housing.

As shown in FIG. 14, the pusher 150 is fully retracted with respect to the housing 14 and the first and second cannulations 46 and 50, such that the tissue receiving gap 62 is at least partially open. The tissue in need of repair is then loaded into the gap 62. For example, for an annulus fibrosus having a fissure, the annulus fibrosus tissue adjacent the defect is inserted into the gap 62 of the suture passer 150. The pusher 150 is then advanced distally with respect to the housing 14. As the pusher 150 is advanced, the pusher body 158 translates within the first cannulation 46, slides through the bore 184 of the shuttling element 155 and into the second cannulation 50. As the pusher 150 advances across the gap 62, the first tissue penetrating end 162 penetrates the tissue received within the tissue receiving gap 62. As shown in FIG. 15, the first tissue penetrating end 162 and the pusher body 158 then translate through the curved portion 54 of the second cannulation 50 and along an upper side of the housing 14. As the pusher 150 continues to translate, the contact surface 178 of the second tissue penetrating end 166 eventually contacts the proximal contact surface 188 of the shuttling element 155, as shown in FIG. 16. With yet further translation of the pusher 150 the second tissue penetrating end 166 pushes/pulls the shuttling element 155 and suture across the tissue receiving gap 62 as shown in FIG. 17. Once the shuttling element 155 has been pushed/pulled to the distal end of the tissue receiving gap 62, the pusher 150 may stop translating.

Figure 19:
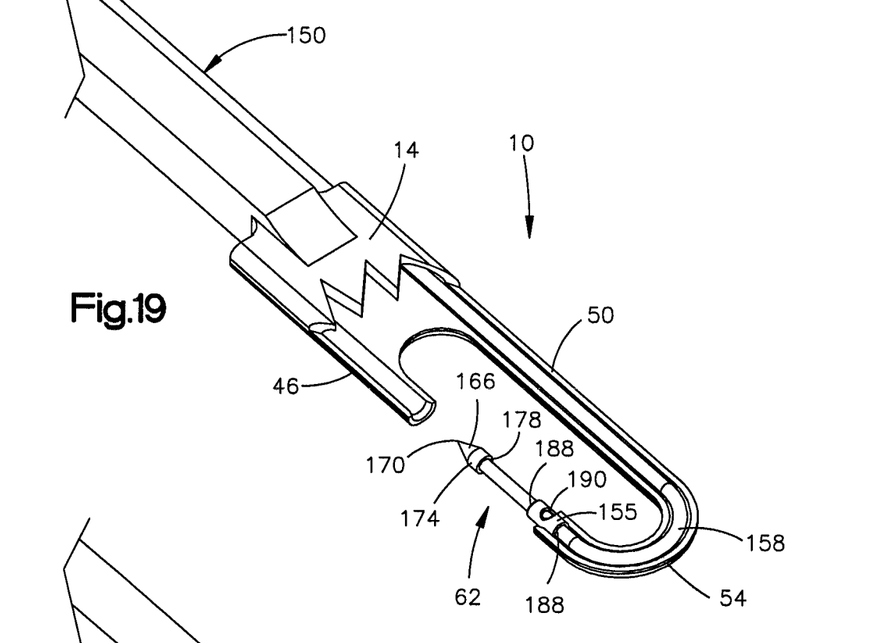
FIG. 19 is an enlarged perspective view similar to FIG. 18, but showing the distal end in a configuration where the pusher is partially advanced back to its original position.
Figure 20:
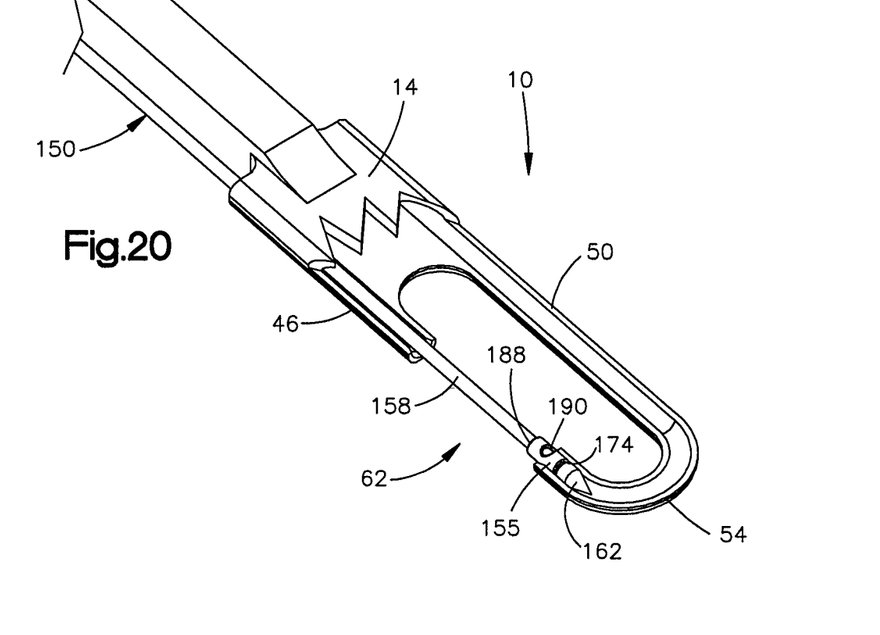
FIG. 20 is an enlarged perspective view similar to FIG. 19, but showing the distal end in a configuration where the pusher is advanced within the housing such that a first end of the pusher abuts the shuttling element.
Figure 21:
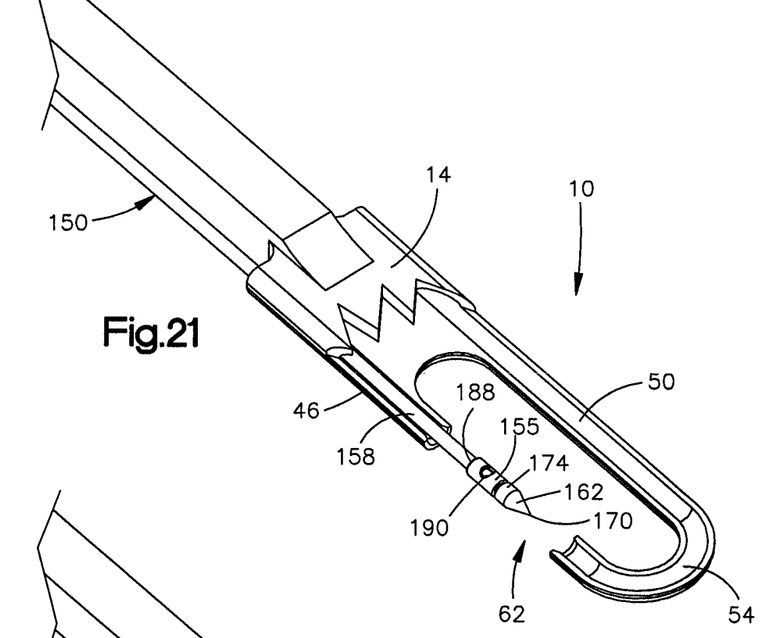
FIG. 21 is an enlarged perspective view similar to FIG. 20, but showing the distal end in a configuration where the pusher pulls the shuttling element across the tissue receiving gap toward its original position.
Figure 22:
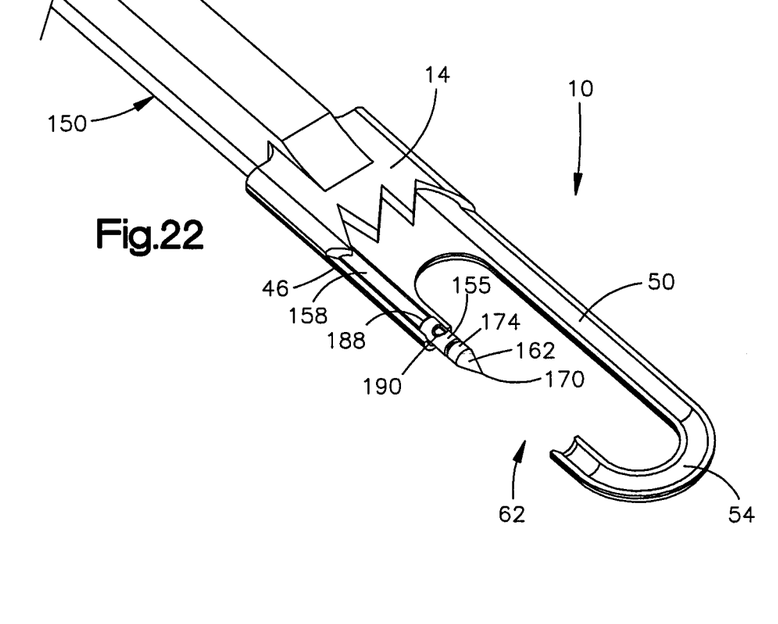
FIG. 22 is an enlarged perspective view similar to FIG. 21, but showing the distal end in its original configuration.

Once the shuttling element 155 has been pushed/pulled to the distal end of the tissue receiving gap, the tissue receiving gap 62 is substantially open, and the bidirectional suture passer 10 is then rotated or moved a small amount with respect to the defect to accommodate a reverse pass of the shuttling element 155 and suture through the gap 62. As shown in FIGS. 18-22, the pusher 150 may then be advanced back through the tissue and toward its original position. In that regard, as the pusher 150 is advanced, the pusher body 158 translates within the second cannulation 50, slides through the bore 184 of the shuttling element 155 and back into the first cannulation 46. Now, as the pusher 150 advances across the gap 62, the second tissue penetrating end 166 penetrates the tissue received within the tissue receiving gap 62. As shown in FIGS. 19 and 20, the first tissue penetrating end 162 and the pusher body 158 then translate back through the curved portion 54 of the second cannulation 50, while the second tissue penetrating end 66 and pusher body 158 translate along a lower side of the housing 14. As the pusher 150 continues to translate, the contact surface 178 of the first tissue penetrating end 162 eventually contacts the distal contact surface 188 of the shuttling element 155, as shown in FIG. 20. With yet further translation of the pusher 150 the first tissue penetrating end 162 pushes/pulls the shuttling element 155 and suture across the tissue receiving gap 62 as best shown in FIG. 20. Once the shuttling element 155 has been pushed/pulled to the proximal end of the tissue receiving gap 62, and the shuttling element 155 is back in its original position, the pusher 150 may stop translating, as best shown in FIG. 22. The bidirectional suture passer 10 is then oriented in a new location with respect to the soft tissue defect, such as by translating or rotating the bidirectional suture passer 10 with respect to the defect, to position a different portion of the soft tissue proximate the defect in the gap 62. The process is repeated one or more times until the tissue is adequately approximated at the defect.

While it is shown in the drawings that the pusher 150 is configured to be manually translated with respect to the housing 14, it is envisioned that a variety of actuation mechanisms can easily be utilized, including automatic, hydraulic, pneumatic, electrical, magnetic, etc. Further, the bidirectional suture passer 10 may be arranged to have a trigger mechanism to actuate the pusher 150.

The suture passer 10, may provide a variety of stitch configurations to approximate the soft tissue defect, including simple stitch, mattress stitch, horizontal box mattress stitch, horizontal mattress stitch, vertical mattress stitch, reverse vertical mattress stitch, or other stitch configurations known in the art. The stitched suture can then be cinched or tensioned across the defect using a pre-tied sliding knot or by tying the opposite ends of the suture strand together.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description. For example, while the first and second push rods 70, 74 are shown as disposed interior to the housing 14 along parallel cannulations, it is envisioned that the first and second push rods 70, 74 can be arranged at oblique or acute angles with respect to one another. Furthermore, while the first and second ends 104, 108 of the shuttling element 92 are described as terminating in needle points that are engagable with recesses disposed at the distal ends of the first and second pushers 70, 74, the small diameter of the shuttling element 92 can allow the first and second ends 104, 108 of the shuttling element 92 to puncture and traverse soft tissue without the inclusion of needle points or to have generally blunt ends.

What is claimed:

1. A suture passing instrument comprising:
a housing having a first cannulation and a second cannulation that is in communication with the first cannulation, such that a tissue receiving gap disposed between the first and second cannulations, the second cannulation having a curved portion;
a pusher including a body, a first tissue penetrating end extending from the body, and a second opposed tissue penetrating end extending from the body, the pusher being translatable within the first and second cannulations of the housing; and
a shuttling element configured to carry a strand of suture across the tissue receiving gap, the shuttling element being slidably coupled to the body of the pusher between the first and second tissue penetrating ends such that the shuttling element is slidable along the body between the first and second tissue penetrating ends,
wherein the shuttling element is configured to be (i) pushed across the tissue receiving gap in a first direction by the first tissue penetrating end and (ii) pushed across the tissue receiving gap in a second direction by the second tissue penetrating end.

2. The suture passing instrument of claim 1, wherein the body of the pusher is made of a flexible material.

3. The suture passing instrument of claim 1, wherein the first and second tissue penetrating ends include opposing contact surfaces, configured to contact respective contact surfaces defined by the shuttling element.

4. The suture passing instrument of claim 1, wherein the body of the pusher is made of a shape memory material.

5. The suture passing instrument of claim 4, wherein the shape memory material is nitinol.

6. The suture passing instrument of claim 1, wherein pusher body has a length that is greater than the length of the tissue receiving gap.

7. The suture passing instrument of claim 1, wherein the shuttling element includes a body that defines a bore, and the pusher body is received within the bore.

8. The suture passing instrument of claim 7, wherein the shuttling element further includes a suture holder.

9. The suture passing instrument of claim 8, wherein the suture holder is an eyelet that is configured to be threaded with the stand of suture.

10. A suture passing instrument comprising:
- a housing having a first cannulation and a second cannulation that is in communication with the first cannulation, such that a tissue receiving gap disposed between the first and second cannulations, the second cannulation having a curved portion;
- a pusher including a body, a first tissue penetrating end extending from the body, and a second tissue penetrating end extending from the body opposite the first tissue penetrating end, the first tissue penetrating end defining a shoulder that has a cross-sectional dimension greater than that of the body, the pusher being translatable within the first and second cannulations of the housing; and
- a shuttling element configured to carry a strand of suture, wherein the shoulder is configured to abut the shuttling element so as to push the shuttling element across the tissue receiving gap when the pusher is translated within the first and second cannulations.

11. The suture passing instrument of claim 10, wherein the shuttling element is slidably coupled to the body of the pusher between the first and second tissue penetrating ends.

12. The suture passing instrument of claim 10, wherein the body of the pusher is made of a flexible material.

13. The suture passing instrument of claim 10, wherein the second opposed tissue penetrating end defines a shoulder that has a cross-sectional dimension greater than that of the body.

14. The suture passing instrument of claim 13, wherein the first and second tissue penetrating ends include opposing contact surfaces, configured to contact respective contact surfaces defined by the shuttling element.

15. The suture passing instrument of claim 13, wherein the shuttling element is pushed across the tissue receiving gap in a first direction by the first tissue penetrating end, and the shuttling element is pushed across the tissue receiving gap in a second direction by the second tissue penetrating end.

16. The suture passing instrument of claim 10, wherein the body of the pusher is made of a shape memory material.

17. The suture passing instrument of claim 16, wherein the shape memory material is nitinol.

18. The suture passing instrument of claim 10, wherein pusher body has a length that is greater than the length of the tissue receiving gap.

19. The suture passing instrument of claim 10, wherein the shuttling element includes a body that defines a bore, and the pusher body is received within the bore.

20. The suture passing instrument of claim 19, wherein the shuttling element further includes a suture holder.

21. The suture passing instrument of claim 20, wherein the suture holder is an eyelet that is configured to be threaded with the stand of suture.

* * * * *